United States Patent
Chen et al.

(10) Patent No.: US 10,555,896 B2
(45) Date of Patent: Feb. 11, 2020

(54) SKIN PENETRATION ENHANCING METHOD AND ITS PENETRATION ENHANCER

(71) Applicant: XIAMEN UNIVERSITY, Xiamen (CN)

(72) Inventors: Ming Chen, Xiamen (CN); Dexiang Wang, Xiamen (CN)

(73) Assignee: XIAMEN UNIVERSITY, Xiamen (CN)

( * ) Notice: Subject to any disclaimer, the term of this patent is extended or adjusted under 35 U.S.C. 154(b) by 0 days.

(21) Appl. No.: 16/028,036

(22) Filed: Jul. 5, 2018

(65) Prior Publication Data

US 2018/0311143 A1 Nov. 1, 2018

Related U.S. Application Data

(63) Continuation of application No. PCT/CN2017/081167, filed on Apr. 20, 2017.

(30) Foreign Application Priority Data

Apr. 27, 2016 (CN) .......................... 2016 1 0267935

(51) Int. Cl.
| | | |
|---|---|---|
| *A61K 9/14* | (2006.01) | |
| *A61K 8/98* | (2006.01) | |
| *A61Q 19/00* | (2006.01) | |
| *A61K 47/46* | (2006.01) | |
| *A61K 9/00* | (2006.01) | |
| *A61M 37/00* | (2006.01) | |
| *A61K 47/24* | (2006.01) | |
| *A61K 31/00* | (2006.01) | |

(52) U.S. Cl.
CPC .............. *A61K 8/98* (2013.01); *A61K 9/0014* (2013.01); *A61K 9/0021* (2013.01); *A61K 47/24* (2013.01); *A61K 47/46* (2013.01); *A61M 37/00* (2013.01); *A61Q 19/00* (2013.01); *A61K 31/00* (2013.01); *A61M 2037/0007* (2013.01)

(58) Field of Classification Search
None
See application file for complete search history.

(56) References Cited

U.S. PATENT DOCUMENTS

2004/0055957 A1   3/2004  Palm et al.
2004/0109872 A1   6/2004  Villani

FOREIGN PATENT DOCUMENTS

| CN | 101626775 A | 1/2010 |
|---|---|---|
| CN | 105858669 A | 8/2016 |
| CN | 105999535 A | 10/2016 |
| KR | 101323613 B1 | 11/2013 |
| WO | WO-2008043071 A2 | 4/2008 |
| WO | 2015156455 A1 | 10/2015 |
| WO | WO-2015156455 A1 | 10/2015 |

OTHER PUBLICATIONS

Jones W.C., Monthly Variations in the Size of Spicules of the Haplosclerid Sponge, Haliclona rosea (Bowerbank), (1991), In: Reitner J., Keupp H. (eds) Fossil and Recent Sponges. Springer, Berlin, Heidelberg, pp. 404-420 (Year: 1991).*
Zhang et al., Skin Delivery of Hydrophilic Biomacromolecules Using Marine Sponge Spicules, (2017), Mol. Pharmaceutics 14:3188-3200 (Year: 2017).*
Wang et al., An Introduction to the Study on Natural Characteristics of Sponge Spicules and Bionic Applications, Advances in Earth Science, Oct. 2006, vol. 21, Issue 10, pp. 1008-1013.
First Office Action in Chinese and English Translation cited in CN Application No. 201610267935.5, dated Nov. 1, 2018, 19 pages.
Second Office Action in Chinese and English Translation cited in CN Application No. 201610267935.5, dated Apr. 16, 2019, 16 pages.

* cited by examiner

*Primary Examiner* — John D Ulm
(74) *Attorney, Agent, or Firm* — Cooper Legal Group, LLC

(57) ABSTRACT

The present invention provides a skin penetration enhancing method and its penetration enhancer which is comprised of sponge spicules or a biologically effective amount of sponge spicules or a combination containing sponge spicules. The penetration enhancer can be applied onto the skin to overcome the skin stratum corneum barrier, which can increase the percutaneous absorption of drugs, vaccines and cosmetics into different skin layers or can improve the transdermal delivery of all these therapeutics into the systemic blood circulation. This technology can be used for dermal delivery of therapeutics into the skin or for transdermal delivery of therapeutics across the skin into systemic blood circulation.

13 Claims, 7 Drawing Sheets

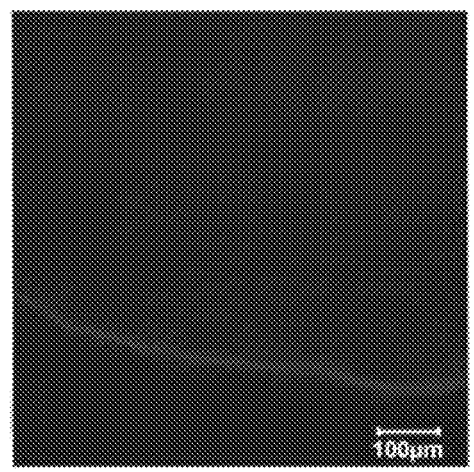 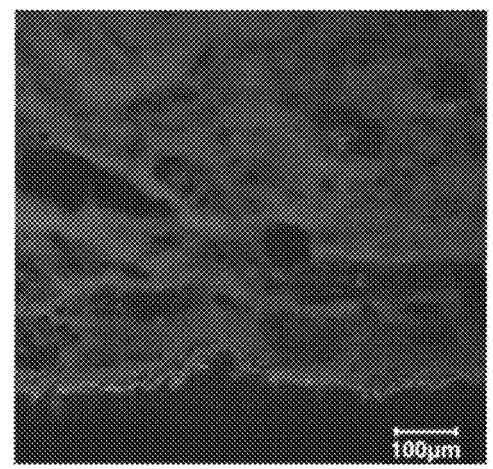
Fig. 3A    Fig. 3B
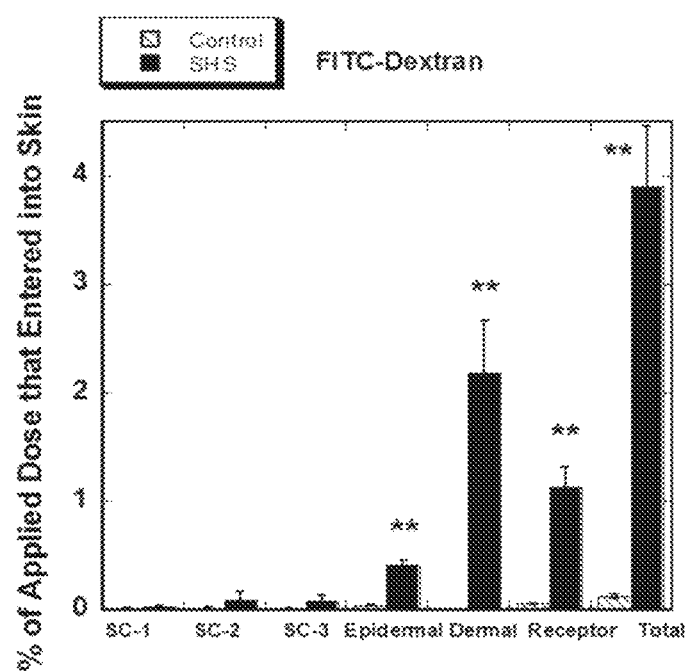
Fig. 4

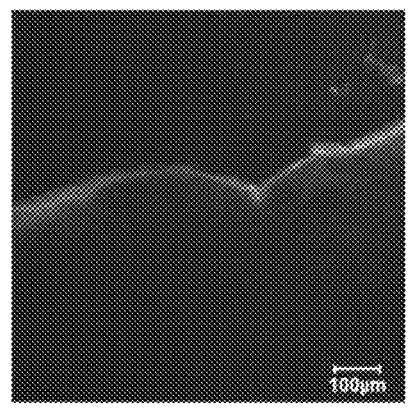
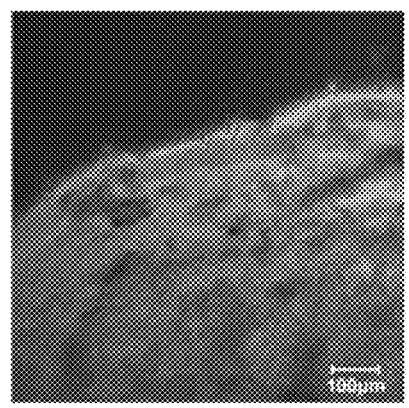
Fig. 5A          Fig. 5B
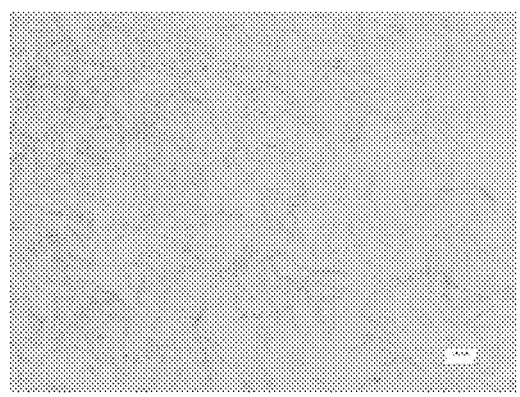
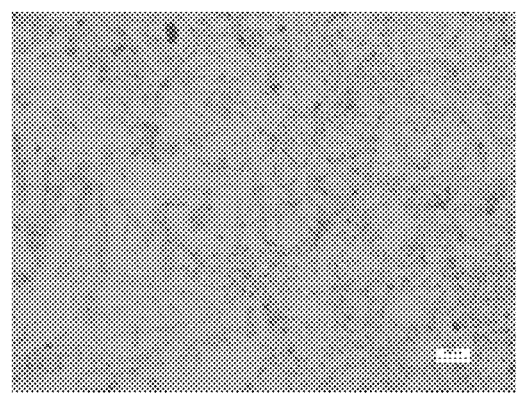
Fig.6A          Fig.6B
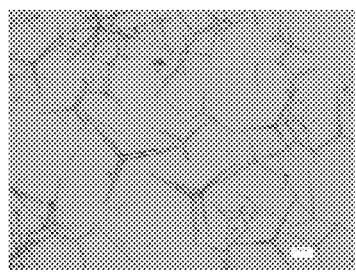
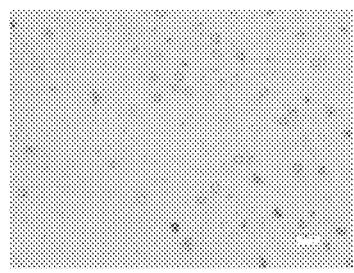
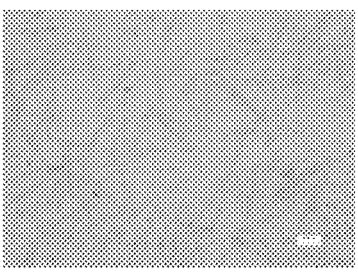
Fig.6C     Fig.6D     Fig.6E

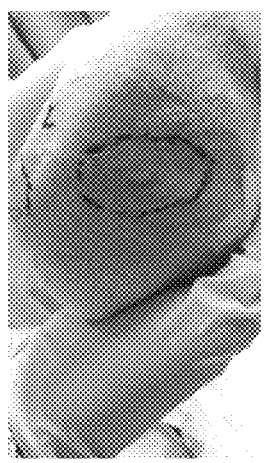 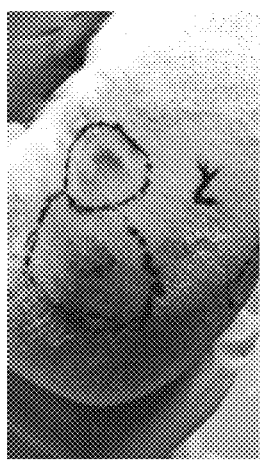 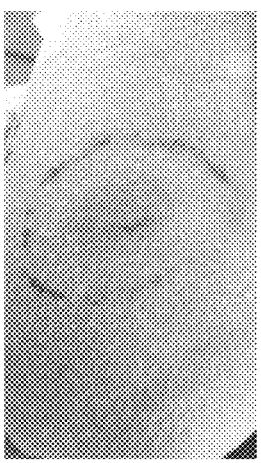 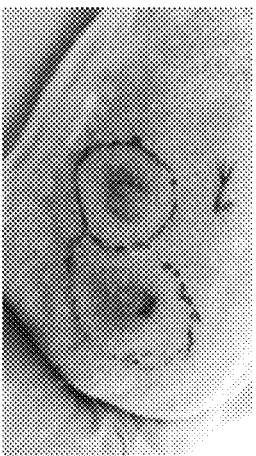
Fig.9A    Fig.9B    Fig.9C    Fig.9D
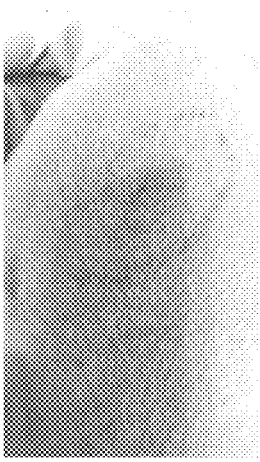 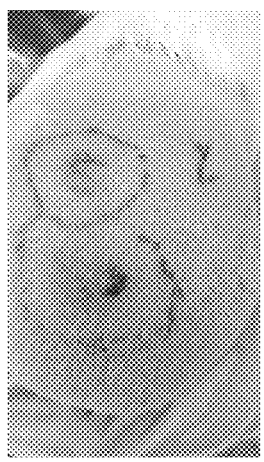 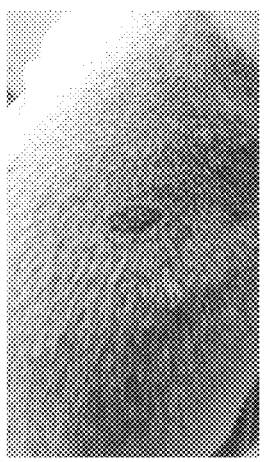 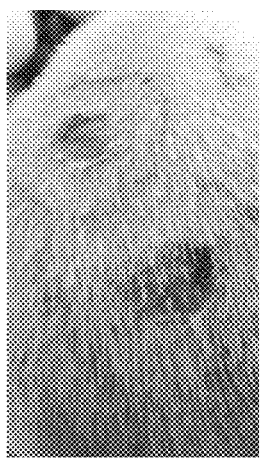
Fig.9E    Fig.9F    Fig.9G    Fig.9H
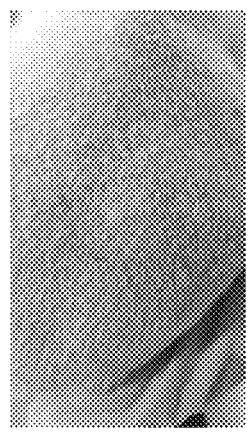 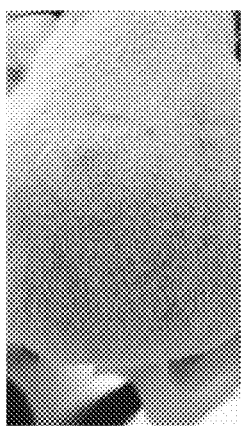 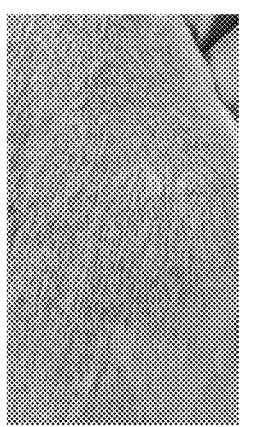 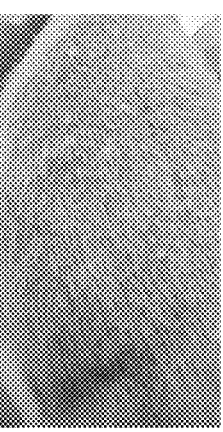
Fig.9I    Fig.9J    Fig.9K    Fig.9L

SKIN PENETRATION ENHANCING METHOD AND ITS PENETRATION ENHANCER

TECHNICAL FIELD

The invention relates to a method and a material for enhancing skin penetration of therapeutics, in particular to sponge spicules as a physical skin penetration enhancer, which increases the percutaneous absorption of therapeutics, including drugs and active ingredients.

BACKGROUND TECHNIQUE

Skin is the largest organ of the human body and offers a direct route for therapeutics delivery. From a pharmaceutical point of view, the skin offers an outstanding route for therapeutic delivery with lots of advantages over other means of administration, including avoidance of first-pass metabolism, sustained and controlled delivery over a prolonged period of time, direct access to local target sites and improved patient compliance. Topical administration is the most challenging in non-invasive route of administration, and it is also the most promising alternative to injection for drug delivery to the diseased region. On the other hand, in the field of medical cosmetology, skin has always been the object of beautification and protection. Skin ageing gradually results in a series of skin problems, including dryness, gloom, wrinkling pigmentation and so on. In order to prevent skin aging or to improve these related symptoms, skin care products can be applied topically. The skin absorption of cosmetic active ingredients is the key for them to exert their specific functions of moisturing, whitening, anti-wrinkle, anti-aging and so on. Therefore, the research on improving the percutaneous absorption of drugs and cosmetic active ingredients is becoming increasingly widespread and the related technologies also have been gradually and widely applied to topical formulations.

However, skin is a biological barrier in essence against the invasion of external pathogens such as bacteria, viruses, or exogenous allergens. In general, only small lipophilic molecules (<500 Da) can penetrate into the skin at therapeutically adequate rates. Therefore, it is quite challenging to deliver various kinds of drugs or active substances with different physical and chemical properties, especially biological macromolecule drugs (polysaccharides, peptides, proteins, biological enzymes, nucleic acids, etc. having a molecular weight of at least $10^4$ Da, $10^5$ Da and even $10^6$ Da) to the deep layers of the skin, which is also the key and focus of the researches in the field of skin drug delivery. So far, the technologies to increase percutaneous absorption of drugs can be generally classified into chemical methods and physical methods. Chemical methods include the use of penetration enhancers, nano-carrier systems (eg, liposomes, microemulsions, polymer nanoparticles, micells, quantum dots, gold nanoparticles), and so on. To marco biomolecules, the penetration enhancing effect from the chemical penetration enhancing techniques is limited. Further, the cytotoxicity and the metabolism in vivo of most chemical penetration enhancers and nanoparticle systems cannot be neglected. Thus, the application and industrialization of the chemical penetration enhancing techniques are restricted. On the other hand, physical penetration enhancing techniques include iontophoresis, ultrasound, electroporation, and microneedles and so on. Many of these techniques result in significant penetration enhancing effects. However, most of them are not portable and can only be applied within small areas of skin. Further, the design and manufacture cost is quite expensive. Thus, the application of physical penetration enhancing techniques is also limited. Among all those enhancement methods, microneedle is a physical penetration enhancing technology emerged in recent years. Microneedles can create plenty of microholes in skin, deep to the epidermis, even to the dermis, providing the most direct and effective way for the absorption of therapeutics. Theoretically, the therapeutics with any molecular size, polarity and other properties can penetrate into the pores formed by the microneedles. When the microneedles are applied to the skin, it is barely painful and the nerve tissue and micro-vessels are generally not injured and the punctured microholes within skin reduce and then close up in short time without causing skin damage.

The manufacturing method of microneedles is maturing day by day, but the choice of microneedle materials is always a problem. The mechanical strength of polymer microneedles is not enough to penetrate the dense stratum corneum; The application of monocrystalline silicon microneedle is limited due to its high brittleness, high manufacturing cost and controversial safety; the metal microneedle is much safer, however, the manufacture cost is quite expensive with the complicated process.

Sponge spicule is siliceous or calcareous fibrous substances as the skeleton in the marine sponge. There are uniaxial, triaxial, and multiaxial types of spicules. At present, most studies on the sponge spicules focus on their nanostructure, optical properties, growth mechanism, regulation, bionics, etc. The application sponge spicules as a skin penetration enhancer to increase percutaneous absorption of drugs and other therapeutics has not yet been fully exploited.

SUMMARY OF THE INVENTION

The object of the present invention is to provide the application of sponge spicules as a physical skin penetration enhancer.

Another object of the present invention is to provide the application of a combination containing sponge spicules as a physical skin penetration enhancer.

The present invention provides a skin penetration enhancer containing sponge spicules or a biologically effective amount of a sponge spicules or a combination containing sponge spicules.

The skin penetration enhancer also contains pharmaceutical therapeutics.

The skin penetration enhancer also contains skin care active ingredients.

The skin penetration enhancer comprises sponge spicules 0.1%-100% (W/W).

The combination containing sponge spicules is a phosphate buffer with the sponge spicules of 10 to 100 mg/mL. The phosphate buffer solution has a concentration of 0.05 M to 0.5 M with the pH of 7.4.

The sponge spicule is derived from *Sponge Haliclona* sp.

The purity of sponge spicules applied for topical administration should be not less than 90%, for example, 95% or more, 98% or more, 99% or more, and most preferably, should be be homogeneous in form and integrated in structure.

The physical skin penetration enhancer can be not only a skin penetration enhancer for drug delivery, but also a skin penetration enhancer for skin care, ingredients absorption, and so on.

One of the methods to apply the sponge spicules as a skin physical penetration enhancer is as follows:

The sponge spicules or the combination containing a biologically effective amount of sponge spicules is applied onto the cleaned skin.

Another method to apply the sponge spicuels as a physical skin penetration enhancer is as follows:

Sponge spicules is added into phosphate buffer to obtain a sponge spicules suspension with a concentration from 10 to 100 mg/mL. The skin is massaged with the spicules suspension described above, the treated area is cleaned, residual sponge spicules are washed out, and the formulations containing therapeutics are then applied to the treated skin area.

The phosphate buffer is a phosphate buffer with a concentration of 0.05M to 0.5M and the pH of 7.4.

The combination containing sponge spicules as a physical skin penetration enhancer can be a drug formulation combination or a cosmetic formulation combination and so on.

The combination containing sponge spicules can be applied directly to the cleaned skin by fingers or other tools (such as an electric massager). The spicules can immediately pierce the skin stratum corneum and make it more permeable, consequently increasing percutaneous absorption of therapeutics involved in the combination.

The application method of sponge spicules to increase the absorption of the cosmetic is as follows:

The sponge spicules are directly applied on the cleaned skin with the massaging by fingers or other massaging tools (such as an electric massager). Then the massage area can be cleaned with saline or water to wash out the residual sponge spicules. And cosmetic formulations can be applied on the treated skin with the sponge spicules to increase the percutaneous absorption of the cosmetic active ingredients.

The massage time and massage intensity can be adjusted as required. For the therapeutics with large molecular weight which is difficult to be absorbed into skin, the massage time or the intensity of massage can be increased. Then the skin can be cleaned and the residual spicules can be washed out by using saline or water. The drug or cosmetic active ingredient can be then topically applied evenly onto the massaged skin. The skin treated with sponge spicules might be fragile due to the formation of a large number of microholes within the surface. Thus it is necessary to protect skin with a moisturizing or sunscreen product. Sponge spicules could stimulate the proliferation of keratinocytes and the synthesis of collagen. Spicules can also result in exfoliation of coenocytes, the skin condition and appearance will be obviously improved.

In the present invention, the sponge spicules are used as a physical skin penetration enhancer to overcome the skin barrier of the stratum corneum and to improve the skin absorption of therapeutics including drugs, vaccines, and cosmetics. Some therapeutics can be dermal delivered into different skin layers, and some of them can be transdermal delivered into systemic blood circulation. The sponge spicules can be applied for both dermal or transdermal drug delivery. It can also be used for skin care products to increase the skin absorption of active ingredients.

DESCRIPTION OF THE DRAWINGS

FIG. 1A—The length of a single sponge spicule, FIG. 1B. Visualization of sponge spicules by microscope, FIG. 1C. Size distribution profile of sponge spicule.

FIGS. 3A-3B is a graph showing the experimental results of the control group and the experiment group of Embodiment 1; FIG. 3A. Control group; FIG. 3B. Experimental group.

FIG. 4 is a histogram of the distribution of FITC-dextran in the skin of Embodiment 2;

FIGS. 5A-5B shows the experimental results of the control group and experimental group of Embodiment 2; FIG. 5A. Control group. FIG. 5B. Experimental group.

FIGS. 6A-6E is a comparison of the morphology of sponge spicules derived from *Haliclona* sp. and sponge spicules derived from the calcareous sponge. the *Tethya* sp. and the *Mycale* sp. (including FIG. 6A high-purity sponge spicules derived from *Haliclona* sp. and FIG. 6B low-purity sponge spicules derived from *Haliclona* sp. FIG. 6C sponge spicules derived from the calcareous sponge. FIG. 6D sponge spicules derived from the *Tethya* sp. FIG. 6E sponge spicules derived from the *Mycale* sp.(the scale in the figure is 100 μm).

(FIG. 8A is the distribution of FITC-Hyaluronic in each skin layer, FIG. 8B is confocal image of skin penetration of FITC-Hyaluronic applied by sponge spicules derived from the *Tethya* sp. FIG. 8C is confocal image of skin penetration of FITC-Hyaluronic applied by sponge spicules derived from the *Haliclona* sp.).

FIGS. 9A-9L show the results of the skin stimulation test of high-purity and low-purity sponge spicule (including FIG. 9A high-purity sponge spicule stimulating the skin 0 h, FIG. 9B low-purity sponge spicule stimulating the skin 0 h, FIG. 9C high-purity sponge spicule stimulating the skin for 24 h, FIG. 9D low-purity sponge spicule stimulating the skin for 24 h, FIG. 9E high-purity sponge spicule stimulating the skin for 48 h, FIG. 9F low-purity sponge spicule stimulating the skin for 48 h, FIG. 9G high-purity sponge spicule stimulating the skin for 96 h, FIG. 9H low-purity sponge spicule stimulating the skin for 96 h, FIG. 9I high purity sponge spicule stimulating the skin for 168 h, FIG. 19J low-purity sponge spicule stimulating the skin for 168 h, FIG. 9K high-purity sponge spicule stimulating the skin 240 h, FIG. 9L low-purity sponge spicule stimulating the skin for 240 h).

DETAILED DESCRIPTION

Figures 1A, 1B:
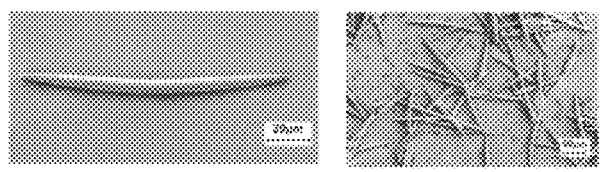
FIGS. 1A-1C shows the morphology and size distribution of the sponge spicule under the microscope.

The invention provides a skin physical penetration enhancer and the useage method for enhancing percutaneous absorption of drugs and active ingredients, which will develop more effective percutaneous methods and percutaneous systems in cosmetic fields and medical fields in the future and promote development of industries. In the present invention, the above summary and the following detailed description of the embodiments are intended to illustrate the present invention more effectively. However, it should be understood that the present invention is not limited to the contents listed herein. Terms and embodiments are used in combination with the embodiments. It is not a limitation of the present invention.

The present invention and its application are specifically described below through embodiments.

Embodiment 1: Fresh porcine skin was punched into a 40 mm diameter disc, subcutaneous adipose tissue was removed and the hair was to be shaved to no more than 2 mm The porcine skin was rinsed with clean water and mounted onto a Franz diffusion cell and all air bubbles between the underside of the skin (dermis) and the buffer in the receptor were completely removed. Add 1 mL of phosphate buffer to the dosing part (15 mm in diameter). The conductivity of the porcine skin will be tested with a waveform generator and a multimeter by applying 100 mV, 100 Hz alternating current. If the current through the porcine skin is less than 5 µA, it demonstrated the skin barrier function was in good condition, and the skin was qualified for experiments. The phosphate buffer was aspirated and 100 µL of phosphate buffer containing 10 mg of sponge spicules was added to the dosing part. The control group was applied with phosphate buffer without sponge spicule. With a mini-massage device or a finger, massaging the drug-applied site for 2 minutes enabled sponge spicules to pierce skin and create micropores. After massage the skin was washed with phosphate buffer or water, to remove the remaining sponge spicules. Then, the conductivity of the porcine skin was measured again, and the current passing through was increased to about 100 µA. The buffer was removed and 150 µL of a solution containing 1.5 mg ANTS-fucoidan (1-30 kDa) was applied evenly over the skin massaged by the sponge spicules. The whole device was then placed in a percutaneous pool containing 37° C. flowing water, while a micromagnetic stir bar was placed in the receptor and rotated at 600 r/min. After incubated for 16 h, the skin was washed five times with phosphate buffer and been removed. Two methods were used to test the penetration enhancing effect of the sponge spicules. (1) A 5 mm diameter piece of skin tissue was punched out at the applied site of skin and immediately frozen in frozen embedding medium. The skin was sectioned at a thickness of 20 µm on a freezing microtome and mounted on a glass slide with permount mounting medium. Confocal microscopy revealed that compared with the control group that massaged without sponge spicules, there were many sponge spicules in the stratum corneum of the experimental group with sponge spicules, and some reached to the depth of dermis. Strong fluorescence was observed in the stratum corneum, epidermis and dermis, indicating that in the skin treated with sponge spicules, the sponge spicules penetrated the skin creating numerous small channels that enhancing the ANTS-fucoidan to penetrate the stratum corneum, acrossing the epidermis and dermis.

(2) The applied site of skin was punched out and 10 layers of stratum corneum were peeled off by tape stripping method, the epidermis layer was scraped and collected, the dermis layer was chopped into pieces. The ANTS-Fucoidan in the first layer of stratum corneum, the second to fifth stratum corneum, the sixth to ten stratum corneum, epidermis and dermis were extracted through soaking the tissues in 4 mL of the mixtures of phosphate buffer and methanol (volume ratio 1:1), at room temperature at 200 r/min. Fluorescence value of ANTS was tested with a a full-wavelength microplate reader, and concentrations of ANTS-Fucoidan in the skin tissue of each layer was obtained according to the standard curve. The results showed that, compared with the control group, the accumulation and distribution of ANTS-fucoidan in each layers of the skin increased with the application of the sponge spicules, especially in the deep layers of the skin. The total transdermal absorption of ANTS-Fucoidan (1-30 kDa) increased from 6.58% to 13.40%.

Figure 1C:
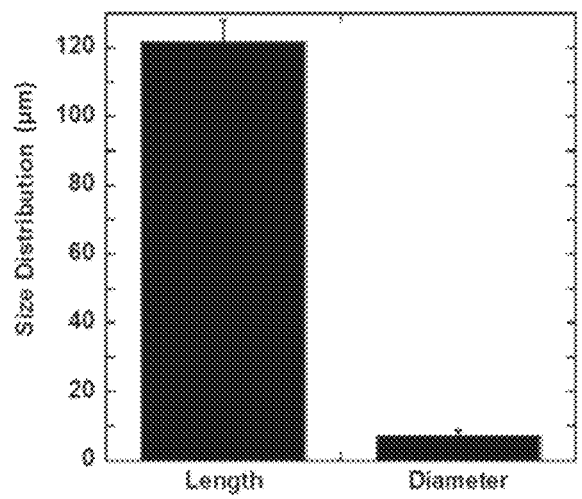
Figure 2:
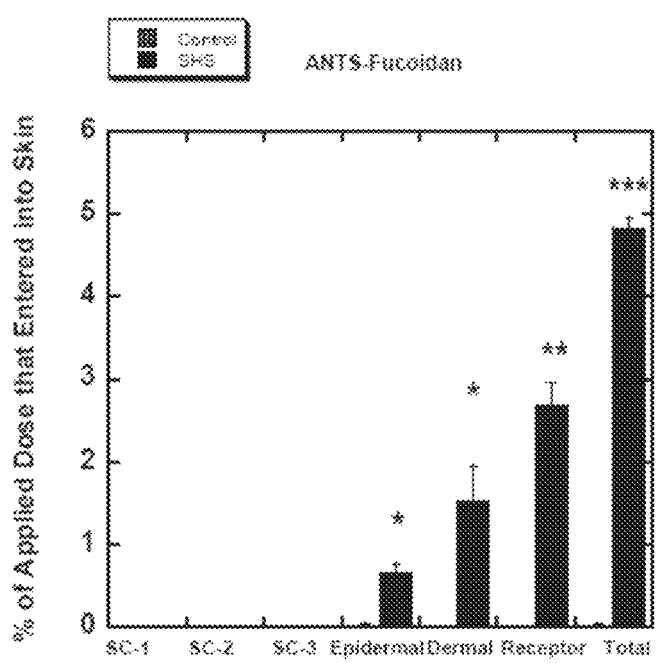
FIG. 2 is a histogram of the distribution of ANTS-fucoidan in the skin of Embodiment 1.

FIG. 1A-1C shows the morphological appearance of a sponge spicule under a microscope; FIG. 2 shows distribution of ANTS-fucoidan in the skin in Embodiment 1. FIGS. 3A-3B shows experimental results of the control group and the experimental group (fluorescence of tissue sections) in Embodiment 1.

Embodiment 2: porcine skin was treated as in Embodiment 1, after the conductivity was measured and the buffer removed, 150 µL of a solution containing 1.5 mg of FITC-Dextran (average molecular weight 10 kDa) and 10 mg of sponge spicule was applied, while the control group was without sponge spicule. Massaging the applied skin with a mini massage device or by manual massage for 2 min. Incubated it in percutaneous pool for 16 h. The same two methods were used to qualitatively and quantitatively detect the transdermal amount of FITC-Dextran, respectively. The confocal microscopic observation results are similar to those in Embodiment 1. Sponge spicules can create numerous micropores on the skin, and the fluorescence intensities of the stratum corneum, epidermis, and dermis of the experimental group were significantly higher than those of the control group. Quantitative results showed that FITC-Dextran that entered the epidermis of the experimental group skin was 17.3 times that of the control group, and FITC-Dextran that entered the dermis was 4.25% of the total dose, while the control group had almost zero in the dermis. It indicated that simultaneous use of the sponge spicules and therapeutics before massage can also enhance the absorption of active ingredients with significant effects.

Embodiment 3: Different Skin Penetration Effects from Species and Morphological Differences FIGS. 6A-6B show the high purity and low purity of the sponge spicules derived from the *Haliclona* sp. used in the present invention, and the morphology of the sponge spicules derived from the the calcareous sponge. the *Tethya* sp. and the *Mycale* sp. As can be seen from the figure, the high-purity (FIG. 6A) and the low-purity (FIG. 6B) sponge spicule derived from the *Haliclona* sp. were both demonstrated as oxeas, and the high-purity sponge spicules derived from the *Haliclona* sp. has a more uniform shape and less impurities. The sponge spicules derived from the calcareous sponge. (FIG. 6C) has a tricuspid shape; the sponges picules derived from the *Tethya* sp. (FIG. 6D) has a spherical shape; and the sponge spicules derived from the *Mycale* sp. (FIG. 6E) has a single sharp shape.

Figure 7:
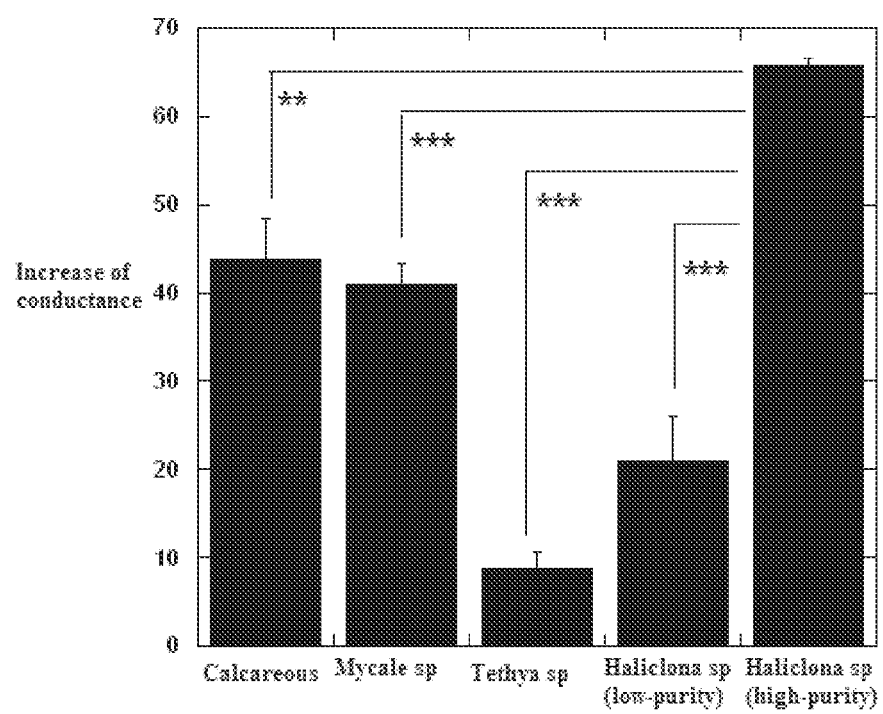
FIG. 7 shows the results of the skin penetration ability of different species and different forms of sponge spicules.

The different types of sponge spicules from different species were used to investigate the effect of promoting penetration. The results are shown in FIG. 7. Under the same conditions, the high-purity (99.5% purity) sponge spicules derived from the *Haliclona* sp. had a much higher increase in conductance before and after the application than the sponge spicules derived from the Calcareous sponge. (purity 95.1%), the *Tethya* sp. (93.2% purity), the *Mycale* sp. (purity 96.7%) and low-purity derived from the *Haliclona* sp. (purity 69.9%), indicating that compared with the above sponge spicules, the high-purity sponge spicules derived from the *Haliconia* sp. has better penetration promoting effect.

Figure 8A:
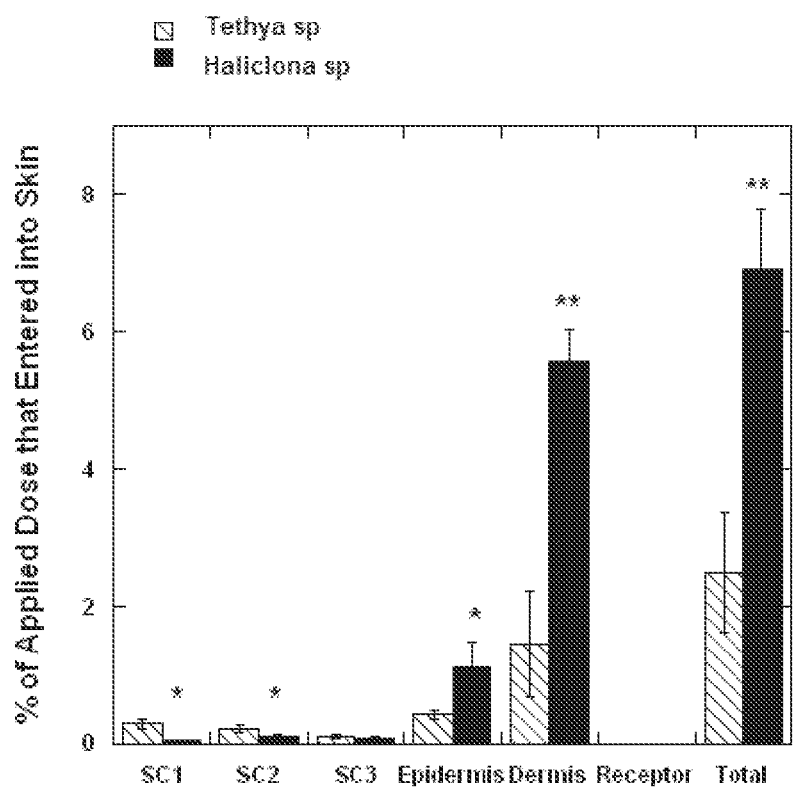
FIGS. 8A-8C are graphs showing the comparison of absorption of FITC-Hyaluronic acid in various layers of the skin after the application of sponge spicules derived from the *Tethya* sp. and high-purity sponge spicules derived from *Haliclona* sp.
Figures 8B, 8C:
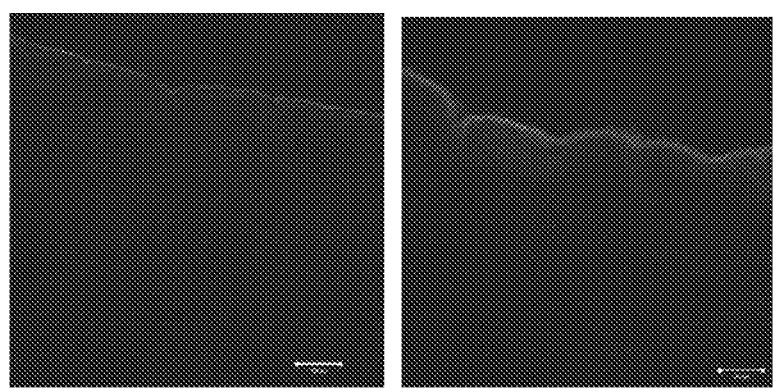
Figure 10:
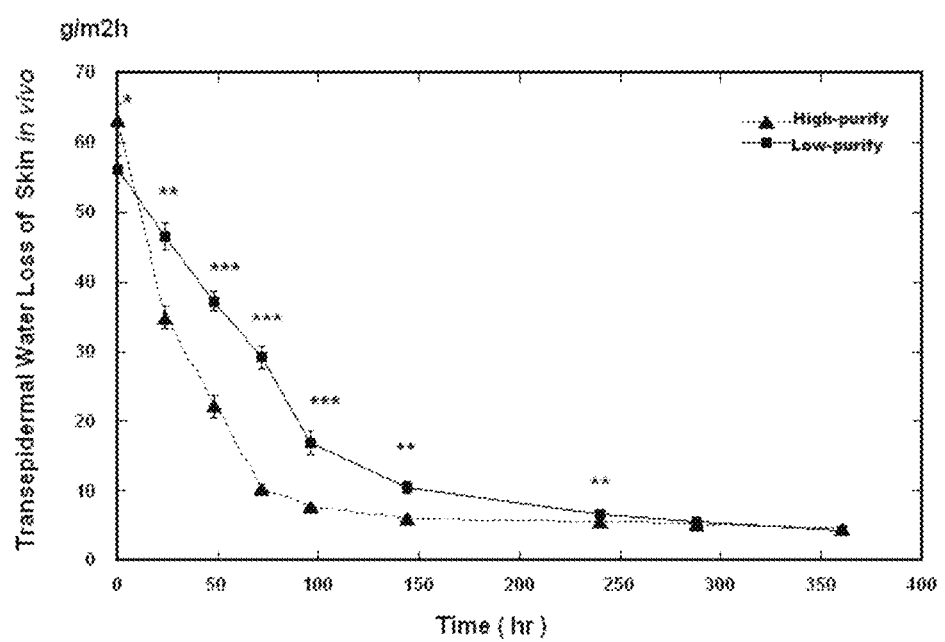
FIG. 10 is a comparison chart of the recovery of skin barrier function over time after stimulating the skin with a high-purity *Haliclona* sp sponge spicules and a low-purity *Haliclona* sp sponge spicules.

Embodiment 4: Difference in Promoting Penetration Effect caused by Purity Differentiation Using a concentration of 1 mg/mL FITC-Hyaluronic acid solution, a concentration of 100 mg/mL (corresponding to a mass concentration of 10%)sponge spicule derived from the *Haliclona* sp. and sponge spicules derived from the *Tethya* sp. solution, the amount of massage was 100 µL. The absorption of FITC-Hyaluronic acid in each layer of the skin was compared between the two kinds of sponge spicules. As shown in FIGS. 8A-8C, the sponge spicule derived from the *Haliclona* sp. has a better permeation effect.

Embodiment 5: Safety Differences Due to Purity Difference

High-purity and low-purity sponge spicules derived from the *Haliclona* sp. were used for skin stimulation experiments. Experimental method: The hair of guinea pig was shaved and 100 µL high-purity (99.5%) and low-purity (69.9%) sponge spicules derived from the *Haliclona* sp. formulation (100 mg/mL equivalent to 10% mass concentration) was massaged on both sides of the back of the guinea pig for two minutes, and 24 hours, 48 hours, 96 hours, 168 hours, and 240 hours later, the transepidermal water loss of guinea pig was measured and photographed respectively.

The results were shown in FIGS. 9A-9L and FIG. 10. The skin recovered basically after 96 hours without any signs of infection in high-purity group. However, in low-purity group, the wounds were redness, showed signs of infection, recovered slowly and basically recovered after 168 hours. The skin itself has an immune system, and the faster it recovers, the less likely it is it is to be infected by external pathogens. The skin stimulated by high-purity sponge spicules recovered faster, indicating that the safety of high-purity sponge spicule derived from the *Haliclona* sp. is better.

The invention claimed is:

1. A skin penetration enhancer, wherein:
the enhancer comprises sponge spicules or a composition containing sponge spicules,
the sponge spicules are derived from sponge *Haliclona* sp,
the composition containing sponge spicules is a phosphate buffer, and
a mass concentration of the sponge spicules in the phosphate buffer is 10-100 mg/mL.

2. The skin penetration enhancer according to claim 1, wherein the enhancer further comprises pharmaceutical ingredients.

3. The skin penetration enhancer according to claim 1, wherein the enhancer further comprises skin care ingredients.

4. The skin penetration enhancer according to claim 1, wherein a weight concentration of the sponge spicules in the enhancer is 0.1%-100%.

5. The skin penetration enhancer according to claim 1, wherein the phosphate buffer is a phosphate buffer with a molar concentration of 0.05 M to 0.5 M and a pH of 7.4.

6. The skin penetration enhancer according to claim 1, wherein the purity of the sponge spicules is not less than 90%.

7. A method for enhancing skin penetration of therapeutics, comprising:
applying sponge spicules or a composition containing sponge spicules onto skin, wherein the sponge spicules are derived from sponge *Haliclona* sp.

8. The method for enhancing skin penetration of therapeutics according to claim 7, wherein the composition containing sponge spicules is a phosphate buffer and a mass concentration of the sponge spicules in the phosphate buffer is 10-100 mg/mL.

9. The method for enhancing skin penetration of therapeutics according to claim 8, wherein the phosphate buffer is a phosphate buffer with a molar concentration of 0.05 M to 0.5 M and a pH of 7.4.

10. The method for enhancing skin penetration of therapeutics according to claim 7, wherein:
the method comprises applying the sponge spicules onto the skin; and
the method further comprises:
massaging an area of the skin onto which the sponge spicules are applied after applying the sponge spicules onto the skin;
cleaning the area of the skin after massaging the area of the skin to remove residual sponge spicules; and
applying a formulation containing therapeutics including a drug or cosmetic active ingredient onto the area of the skin previously treated with the sponge spicules.

11. The method for enhancing skin penetration of therapeutics according to claim 8, wherein:
the method comprises applying the composition containing sponge spicules directly onto the skin; and
massaging an area of the skin onto which the composition containing sponge spicules is applied after applying the composition containing sponge spicules.

12. The method for enhancing skin penetration of therapeutics according to claim 7, further comprising:
applying ANTS-Fucoidan onto an area of the skin onto which the sponge spicules or the composition containing sponge spicules are applied after applying the sponge spicules or the composition containing sponge spicules.

13. The method for enhancing skin penetration of therapeutics according to claim 7, further comprising:
applying FITC-Dextran onto an area of the skin onto which the sponge spicules or the composition containing sponge spicules are applied simultaneously with applying the sponge spicules or the composition containing sponge spicules.

* * * * *